United States Patent [19]

Köhler et al.

[11] Patent Number: 5,250,742
[45] Date of Patent: Oct. 5, 1993

[54] PROCESS FOR THE PRODUCTION OF PROPARGYL ETHERS AND NEW PROPARGYL ETHERS

[75] Inventors: Burkhard Köhler; Ralf Dujardin; Wolfgang Ebert, all of Krefeld, Fed. Rep. of Germany

[73] Assignee: Bayer Aktiengesellschaft, Leverkusen, Fed. Rep. of Germany

[21] Appl. No.: 908,460

[22] Filed: Jul. 6, 1992

[30] Foreign Application Priority Data

Jul. 16, 1991 [DE] Fed. Rep. of Germany ....... 4123535

[51] Int. Cl.$^5$ .......................................... C07C 43/215
[52] U.S. Cl. .................................... 568/640; 568/646
[58] Field of Search .................. 568/640, 646, 633

[56] References Cited

U.S. PATENT DOCUMENTS

| | | | |
|---|---|---|---|
| 2,331,265 | 11/1940 | Coleman | 568/640 |
| 3,340,308 | 9/1967 | Sterling | 568/640 |
| 4,885,403 | 12/1989 | Inbasekaran et al. | 568/640 |

FOREIGN PATENT DOCUMENTS 0293768 12/1988 European Pat. Off. .
2432009 2/1980 France .

OTHER PUBLICATIONS

S. K. Dirlikov, "Propargyl-terminated Resins—A Hydrophobic Substitute for Epoxy Resins"; *High Performance Polymers*, vol. 2, No. 1, (1990), pp. 67-77.

Chemical Abstracts, vol. 110, No. 1, Jan. 2, 1989, abstract No. 7833x, K. Yamataka et al. "Process for the preparation of aromatic ethers", p. 715; & JP-A-63 104 936 (Asahi Chem. Ind. Co.).

Chemical Abstracts, vol. 70, No. 9, Mar. 3, 1969, abstract No. 37178k, "Allyl hydrocarbyl ethers", p. 278; & IT-A-802 417 (Montecatini Edison), Feb. 15, 1968.

*Primary Examiner*—Marianne M. Cintins
*Assistant Examiner*—Margaret J. Page
*Attorney, Agent, or Firm*—Connolly & Hutz

[57] ABSTRACT

The invention relates to a process for the production of new propargyl ethers in the presence of iron as catalyst and to new propargyl ethers.

3 Claims, No Drawings

PROCESS FOR THE PRODUCTION OF PROPARGYL ETHERS AND NEW PROPARGYL ETHERS

This invention relates to a process for the production of new propargyl ethers in the presence of iron as catalyst and to new propargyl ethers.

Propargyl ethers are of interest for the production of hydrophobic thermosets which combine the advantages of epoxy resins with the advantage of low water absorption. This class of thermosets and conventional processes for preparing the propargyl ethers used as structural units are described in High Performance Polymers 2(1) (1990), 67-77. Some of these processes lead to the formation of unwanted Claisen rearrangement products while other processes require long reaction times.

Accordingly, there is an interest in processes which can be carried out under moderate conditions with short reaction times.

In addition, new propargyl ethers containing a large percentage of cycloaliphatic groups which would allow the production of potentially even more hydrophobic thermosets would also be of interest.

It has now surprisingly been found that the reaction of phenols, bisphenols or polyphenols with propargyl halides is accelerated by the addition of iron or iron compounds.

Accordingly, the present invention relates to a process for the production of aromatic propargyl ethers in which phenolic compounds, preferably mono-, di- or polyphenols, are reacted with 1 to 2 mol propargyl halide per mol phenolic OH group in the presence of 1 to 2 mol base per mol phenolic OH groups in solvents, preferably in aliphatic $C_{1-4}$ alcohols, such as isopropanol for example, or in ketones, such as for example acetone, methyl ethyl ketone, cyclohexanone, or in nitriles, such as acetonitrile for example, or in amides, such as for example dimethyl formamide or dimethyl acetamide, or in lactams, such as for example N-methyl pyrrolidinone, N-methyl caprolactam, or in ureas, such as for example tetramethyl urea, N,N'-dimethyl propylene urea, N,N'-dimethyl imidazolidinone, or in dimethyl sulfoxide, characterized in that 0.001 to 0.01 mol per mol OH groups of iron is added to the reaction solution in elemental form or in the form of iron compounds, preferably iron(II) salts or iron(III) salts, such as for example oxides, sulfides, halides, nitrates, sulfates, formates, oxalates, tartrates, acetates, aliphatic $C_{3-22}$ carboxylates, aromatic $C_{6-14}$ carboxylates, and more preferably in the form of an iron compound soluble in the reaction solvent.

The present invention also relates to new propargyl ethers corresponding to general formula I

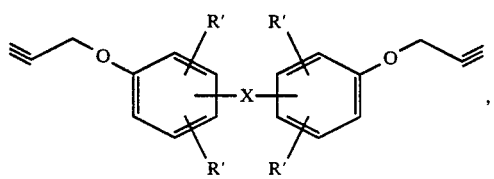

in which
R' represents hydrogen or methyl and
X represents the substituents

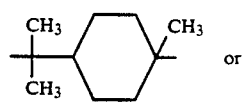

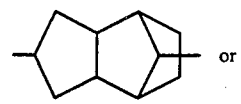

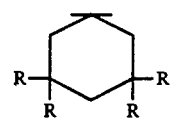

in which
R is hydrogen or $C_{1-22}$ alkyl.

The preferred substituent is the substituent corresponding to formula (IV). The new propargyl ethers are preferably obtained by the process according to the invention.

Examples of monophenols which may be reacted in accordance with the invention are phenol, cresols, xylenols, 2- or 4-phenyl phenol, octyl phenols, nonyl phenols, dodecyl phenols, 2-hydroxybenzaldehyde, 4-hydroxybenzaldehyde, 2-, 3- or 4-hydroxybenzoic acid r esters or amides thereof, 4-hydroxycinnamic acid or esters or amides thereof.

Examples of diphenols which may be reacted in accordance with the invention are bishydroxyphenol methanes (all possible isomers), 2,2-bis-(4-hydroxyphenyl)-propane, 2,2-bis-(4-hydroxyphenyl)-hexafluoropropane, hydroquinone, resorcinol, pyrocatechol, 4,4'-dihydroxybiphenyl, 2,2'-dihydroxybiphenyl, dihydroxyterphenyl, dihydroxyquaterphenyl, 4,4'- or 3,3'-dihydroxydiphenyl ether, 4,4'-dihydroxydiphenyl sulfone, 4,4'-dihydroxydiphenyl sulfide, 3,4- or 2,4-dihydroxybenzaldehyde, 2,4- or 2,4'- or 4,4'-dihydroxybenzophenone, 2,4- or 3,4-dihydroacetophenone, 4,4'-dihydroxystilbene, 1,2-bis-(4-hydroxyphenol)-ethane, 1,2-bis-(4-hydroxyphenyl)-propane.

Examples of diphenols which may be reacted in accordance with the invention (the reaction leading to the propargyl ethers according to the invention containing a large percentage of cycloaliphatic groups) are bis-(4-hydroxyphenyl)-cyclohexane, 1,1-bis-(4-hydroxyphenyl)-3,3,5-trimethyl cyclohexane, condensation products of phenol and dicyclopentadiene, condensation products of phenol and terpenes, such as limonene for example, more preferably 1,1-bis-(4-hydroxyphenyl)-3,3,5-trimethyl cyclohexane.

Examples of polyphenols which may be reacted in accordance with the invention are condensation products of formaldehyde and phenols, such as novolaks for example.

Examples of bases which may be used in accordance with the invention are alkali metal alcoholates, alkali metal carbonates, alkali metal hydroxides, tertiary amines or basic ion exchangers.

Examples of solvents used in accordance with the invention are methanol, ethanol, n-propyl alcohol, isopropyl alcohol, butanols, acetone, cyclohexanone, acetonitrile.

The process according to the invention may be carried out over a period of 0.1 to 10 hours and preferably over a period of 0.5 to 5 hours at temperatures of 0° to 100° C. and preferably 20° to 80° C. and under a pressure of 0.5 to 10 bar and preferably under normal pressure.

It is distinguished by a high reaction velocity. In addition, unwanted rearrangements occur to only a minimal extent.

The propargyl ethers according to the invention with a large percentage of cycloaliphatic groups are distinguished by good solubility both in polar solvents, such as isopropanol for example, and in apolar solvents, such as petroleum ether for example. Their good solubility facilitates processing to glass-fiber- or carbon-fiber-reinforced thermoset components, for which purpose the reinforcing fibers have to be impregnated beforehand with a monomer solution.

EXAMPLES

Comparison Example 1

Preparation of 4-proparyloxybenzaldehyde 122 g 4-hydroxybenzaldehyde, 1,000 ml acetone, 138 g potassium carbonate and 150 g propargyl bromide are mixed. The mixture is heated for 4 hours to 60° C., precipitated constituents are filtered off and, after concentration, the reaction product is taken up in methylene chloride, extracted by shaking with 10% NaOH and the organic phase is concentrated. 20 to 35 g 4-propargyloxybenzaldehyde.

Example 1

(process according to the invention)

Preparation of 4-propargyloxybenzaldehyde

The procedure is as described in Comparison Example 1, except that 0.05 g iron(III) chloride is added to the mixture. 109 g 4-propargyloxybenzaldehyde are obtained in NMR-pure form.

Example 2

(Process according to the invention)

Preparation of 2,2-bis-(4-propargyloxyphenyl)-propane 228 g bisphenol A, 300 ml isopropanol, 360 g of a 30% solution of sodium methanolate in methanol, 0.05 g iron-(III) chloride and 200 g propargyl chloride are mixed. An exothermic reaction takes place, most of the product having been formed (TLC verification) by the time the reaction is over (approx. 15 minutes). The reaction mixture is left to react for 4 hours and is then filtered and concentrated. 275 g of the product (characterized by NMR spectroscopy) are obtained.

Example 3

(Propargyl ether containing a large percentage of cycloaliphatic groups)

Preparation of 1,1-bis-(4-proparyloxyphenyl-3,3,5-trimethyl cyclohexane

The procedure is as described in Example 2 except that the bisphenol A is replaced by 319 g 1,1-bis-(4-hydroxyphenyl)3,3,5-trimethyl cyclohexane. 326 g product (characterized by NMR spectroscopy) are obtained.

What is claimed is:

1. Propargyl ethers corresponding to general formula I

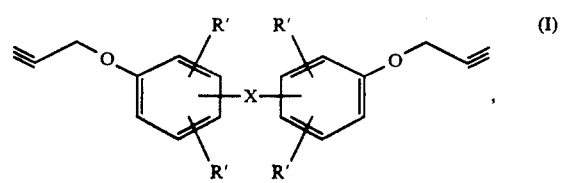

in which
R' represents hydrogen or methyl and
X represents the substituent

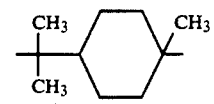

2. Propargyl ethers corresponding to general formula I

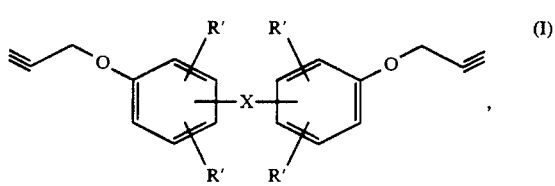

in which
R' represents hydrogen or methyl and
X represents the substituent

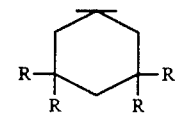

in which
R is $C_{1-22}$ alkyl.

3. Propargyl ethers corresponding to general formula I

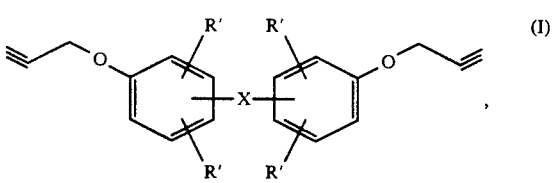

in which
R' represents hydrogen or methyl and
X represents the substituent

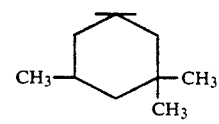

* * * * *